US006478825B1

(12) United States Patent
Winterbottom et al.

(10) Patent No.: US 6,478,825 B1
(45) Date of Patent: Nov. 12, 2002

(54) IMPLANT, METHOD OF MAKING SAME AND USE OF THE IMPLANT FOR THE TREATMENT OF BONE DEFECTS

(75) Inventors: John M. Winterbottom, Jackson, NJ (US); Lawrence Shimp, Morganville, NJ (US); Todd M. Boyce, Aberdeen, NJ (US); David Kaes, Toms River, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 09/996,243

(22) Filed: Nov. 28, 2001

(51) Int. Cl.$^7$ .................................................. A61F 2/36
(52) U.S. Cl. ................................................ 623/23.63
(58) Field of Search .......................... 623/23.51, 23.53, 623/23.61, 23.63

(56) References Cited

U.S. PATENT DOCUMENTS

| 5,086,401 A | | 2/1992 | Glassman et al. |
| 5,439,951 A | * | 8/1995 | Glimcher et al. |
| 5,683,461 A | | 11/1997 | Lee et al. |
| 5,814,328 A | | 9/1998 | Gunasekaran |
| 5,899,939 A | | 5/1999 | Boyce et al. |
| 6,117,456 A | | 9/2000 | Lee et al. |
| 6,123,731 A | | 9/2000 | Boyce et al. |
| 6,162,258 A | * | 12/2000 | Scarborough et al. |

FOREIGN PATENT DOCUMENTS

JP 252347 * 9/2001

OTHER PUBLICATIONS

Stevenson et al., "Factors Affecting Bone Graft Incorporation", Clinical Ortho. and Related Res., No. 323, pp. 66–74 (1996).
Buttermann et al., "The Use of Bone Allografts in the Spine", Clinical Ortho. and Related Res., No. 324, pp. 75–78, (1996).
Nimni, "Collagen", Biotechnology, vol. III, pp. 19–24 (1988).
Reddi et al., "Biochemical Sequences in the Transformation of Normal Fibroblasts in Adolescent Rats", Proc. Nat. Acad. Sci. USA, vol. 69, No. 6, pp. 1601–1605 (1972).
Lewandrowski et al, "Kinetics of cortical bone demineralization: Controlled demineralization—a new method for modifying cortical bone allografts", J. Bio. Material Res., vol. 31, pp. 365–372 (1996).

* cited by examiner

*Primary Examiner*—Ralph A. Lewis
(74) *Attorney, Agent, or Firm*—Dilworth & Barrese, LLP (57) ABSTRACT

An implant is provided as a solid aggregate of bone-derived elements, e.g., particles, powders, granules, fibers, strips and/or large pieces of xenogenic, allogenic, transgenic, tissue engineered or autologous cortical and/or cancellous bone, employing as binding agent for the bone-derived elements a precipitate or crystalline bridge of metal oxide, metal hydroxide, metal salt of an inorganic acid, metal salt of an organic acid, metal-containing silica based glass, or mixture thereof, the binding agent possessing at least slight solubility in polar solvent, adjacent bone-derived elements being bonded to each other through engagement with particles or bridge-like structures of bonding agent.

39 Claims, 2 Drawing Sheets

IMPLANT, METHOD OF MAKING SAME AND USE OF THE IMPLANT FOR THE TREATMENT OF BONE DEFECTS

BACKGROUND OF THE INVENTION

1. Field of the Invention

The present invention relates to an implant for use in the repair, replacement and/or augmentation of tissue, including various portions of animal or human skeletal systems, and to a method for manufacturing the implant. More particularly, this invention relates to an implant made up of a solid aggregate of bone-derived elements, the manufacture of the implant and its use in the repair of bone defects.

2. Description of the Related Art

The use of autograft bone, allograft bone or xenograft bone is well known in both human and veterinary medicine. See Stevenson et al., *Clinical Orthopedics and Related Research*, 323, pp. 66–74 (1996); Buttermann et al., "The Use of bone allografts in the spine", *Clinical Orthopedics and Related Research*, 324, pp.75-85 (1996). In particular, transplanted bone is known to provide support, promote healing, fill bony cavities, separate bony elements such as vertebral bodies, promote fusion and stabilize the sites of fractures. More recently, processed bone has been developed into shapes for use in new surgical applications, or as new materials for implants that were historically made of non-biologically derived materials.

Bone is made of several endogenous constituents, including collagen, hydroxyapatite and several active proteins. When used as a biomaterial, these components of the bone can provide advantageous biological and mechanical properties. Such properties may be enhanced by processing treatments and/or the addition of one or more medically useful substances to the bone.

Allograft bone has been demonstrated, over the course of several decades, to provide significant clinical advantages in the treatment of certain orthopedic, podiatric, oral, maxillofacial, dental, and other skeletal diseases. Unlike other implants used in skeletal sites, allograft bone implants have the capacity to participate in bony healing at the site of surgery, through the events of callous formation and wound healing, and osteonal remodeling. Cortical allograft implants, however, remodel slowly over the course of months to years, and all bone allografts have been limited to shapes and sizes dictated by the limits of the initial starting bone tissue.

One known type of allograft bone implant involves treatment of the bone with gluteraldehyde and/or proteoglycan removal in order to induce calcification in the implant. This treated implant is then placed in a solution of simulated body fluid so as to induce calcification. See Nimni et al., "Collagen", Vol 3, Biotechnology, pp.20–23, CRC Press, Boca Raton, Fla. (1998).

U.S. Pat. No. 5,899,939 describes a bone-derived implant made up of one or more layers of fully mineralized or partially demineralized cortical bone which are assembled into a unitary structure to provide an implant exhibiting good overall load-supporting properties.

U.S. Pat. No. 6,123,731 describes an implant fabricated from a solid aggregate of bone-derived elements possessing chemical linkages between their adjacent surface-exposed collagen. Other components can be incorporated into the bone implant material such as bone-growth inducing substances, growth factors, etc.

SUMMARY OF THE INVENTION

The present invention provides an implant which can potentially utilize the natural healing capacities of bone tissue and which can be formed with a range of geometries, internal porosity and architectures. The advantageous features of the implant include the ability to approximate the internal architecture and porosity of natural bone thereby providing the capability to improve the biological healing response. Implants with allograft properties can be made to shapes and sizes that are not limited by the geometry of the bone from which they are made and can provide a stock material for subsequent shaping to fit a particular bone repair site.

It is an object of the invention to provide an implant made up of bone-derived elements that are made to adhere to each other so as to provide a solid aggregate whose mechanical and biological properties approach those of healthy bone.

It is a particular object of the present invention to provide an implant made up of a solid aggregate of bone-derived elements which are bonded to each other through their engagement with a biocompatible nonadhesive binding agent.

It is another object of this invention to provide an implant which can optionally include one or more medically/surgically useful substances such as bone-growth inducing substances, growth factors, etc.

It is yet another object of the invention to provide an implant possessing a network of pores, perforations, apertures, channels or spaces which permits and encourages penetration by endogenous and exogenous bone healing materials and blood supply, and simultaneously provides a means for incorporating one or more bone healing substances.

It is still a further object of the present invention to provide an implant which can be fashioned into a variety of shapes and sizes which are not limited by constraints imposed by the size and/or types of donor bone which are available for the construction of the implant.

It is also an object of the invention to provide a method of manufacturing an implant which will provide a strong, biocompatible implant of any size and/or shape for implantation.

In keeping with these and other objects of the invention, there is provided an implant which comprises a solid aggregate of bone-derived elements in which the surfaces of individual bone-derived elements possess one or more binding agents selected from the group consisting of metal oxide, metal hydroxide, metal salt of an inorganic acid, metal salt of an organic acid and metal-containing silica-based glass, the binding agent possessing at least slight solubility in a polar solvent, adjacent bone-derived elements in the aggregate being bonded to each other through engagement with the binding agent.

Further in keeping with the invention, there is provided a method of making an implant made up of a solid aggregate of bone-derived elements which comprises:

a) contacting the surfaces of a quantity of bone-derived elements with a polar solvent solution of binding agent selected from the group consisting of metal oxide, metal hydroxide, metal salt of an inorganic acid, metal salt of an organic acid and metal-containing silica-based glass.

b) forming the bone-derived elements into an aggregate prior to or following contacting step (a); and, c) removing polar solvent from the aggregate of bone-derived elements to provide the implant, the surfaces of individual bone-derived elements in the implant possessing binding agent with adjacent bone-derived elements being bonded to each other through engagement with the binding agent.

The implant of this invention is intended to be used in the repair of any of a variety of bone defects where it can facilitate healing through one or more osteogenic, osteoconductive and/or osteoinductive mechanisms. The bone-derived implant, or osteoimplant, of the present invention can be made to approximate the mechanical strength characteristics of natural bone and to permit gradual transfer of load-bearing support therefrom to newly formed bone tissue over time.

The term "osteogenic" as used herein shall be understood to refer to the ability of a substance to induce new bone formation via the participation of living cells from within the substance.

The term "osteoconductive" as used herein shall be understood to refer to the ability of a substance or material to provide surfaces that are receptive to the growth of new host bone.

The term "osteoinductive" as used herein shall be understood to refer to the ability of a substance to recruit cells from the host which have osteogenic potential and the ability to form ectopic bone.

The expression "bone-derived elements" as used hereinafter shall be understood to refer to pieces of bone in any of a variety of sizes, thicknesses and configurations, including monolithic segments of bone, thin to thick bone sheets and smaller pieces of bone such as powders, particles, granules, fibers, strips, etc., which can be obtained by milling, slicing, cutting or machining whole bone. Such elements can be fully mineralized, partially demineralized or fully demineralized.

The term "biocompatible" and expressions of like import shall be understood to mean the absence of unacceptable detrimental biological response, e.g., stimulation of a severe, long-lived or escalating biological response to an implant and is distinguished from a mild, transient inflammation which accompanies implantation of essentially all foreign objects into a living organism and is also associated with the normal healing response. Thus, materials which alone in appropriate quantities are generally considered nonbiocompatible can be considered biocompatible within the aforestated meaning if present in small enough quantities such that they do not elicit a significant level of undesirable or detrimental tissue response.

The term "engagement" is used herein to define the nature of the bonding of adjacent bone-derived particles as achieved either by the interlocking of mutually contacting particles of binding agent present on the surfaces of adjacent bone-derived elements and/or by bridge-like structures of binding agent spanning gaps between adjacent bone-derived elements. Accordingly, the engagement of adjacent bone-derived elements with the binding agent in accordance with the present invention can be thought of as largely mechanical in nature. Specific preferred examples include inter-element crystalline bridges induced either by precipitation reaction or by solid state crystal nucleation.

The term "nonadhesive" shall be understood to exclude known and conventional "adhesives", the latter term being reserved for materials that achieve bonding of substrates primarily by means of electrical forces, molecular forces such as van der Waals forces or diffusion into the substrates, e.g. as is the case with the in situ formed acrylate adhesives that heretofore have been used in the making and/or installation of implants for the repair of bone defects. Examples of non-adhesive biocompatible binding agents include crystalline calcium phosphates such as hydroxyapatite, poorly crystalline hydroxyapatite or dicalcium phosphate dihydrate each of which is among the useful binding agents herein.

The expression "endogenous binding agent" refers to a generally crystalline binding agent produced when salts endogenous to bone are induced to recrystallize as the same salt, or a different phase of the same material, or as a precipitate following a reaction between an exogenous and an endogenous material. Such recrystallizations may be solvent-mediated or occur in the solid phase.

BRIEF DESCRIPTION OF THE PHOTOMICROGRAPHS

DESCRIPTION OF THE PREFERRED EMBODIMENTS

The implant of the present invention comprises a quantity of bone-derived elements which are bonded together to provide a solid, coherent aggregate through engagement with particles of binding agent present on the surfaces of the bone-derived elements constituting the implant. In most embodiments, the binding agent will be biocompatible.

The bone-derived elements can vary in size from fairly large, or monolithic, whole bone pieces and sheets to fairly small bone pieces such as particles, granules, powders, fiber-like pieces, strips, etc. In the case of monolithic bone pieces, e.g., those representing a diaphyseal cut of a long bone, slabs cut from cortical bone, struts, cancellous blocks, etc., the size of the pieces can range from about 0.5 mm to about 30 cm along their greatest dimension. Bone sheets will often be rectangular in shape, e.g., from about 1 to about 30 cm in length and from about 5 mm to about 15 cm in width, with a thickness of from about 0.1 mm to about 10 mm. Relatively small bone pieces such as the aforementioned bone, powders, particles, granules, etc., will generally range from about 0.0001 mm to about 5 mm, preferably about 0.01 mm to about 1 mm, along their greatest dimension and fiber-like pieces and strips will have lengths ranging from about 1 cm to about 30 cm with length-to-width ratios of from about 3:1 to about 20:1. All combinations of the foregoing bone-derived elements are contemplated for the manufacture of a given implant in accordance with the invention.

The bone-derived elements typically exhibit osteogenic, osteoconductive and/or osteoinductive properties and can be derived from xenogenic, allogenic, autologous, transgenic and/or tissue-engineered bone. For many of the applications herein, allogenic human bone, i.e., donated human bone, including both cortical and cancellous varieties, is preferred.

The binding agent, which, as stated above, effects the bonding of adjacent bone-derived elements making up the implant of the invention through mechanical engagement of their mutually contacting particles or by bridge-like structures of binding agent between adjacent bone-derived elements, is selected from amongst the metal oxides, metal hydroxides, metal salts of inorganic acids, metal salts of organic acids and metal containing silica-based glasses. The metal contained in the binding agent can be of endogenous origin, e.g., calcium derived from bone, of exogenous origin, i.e., calcium or other metal from a source other than that of bone, or a mixture of the foregoing. The metal is preferably a divalent metal and of these, the alkaline earth metals, particularly calcium, are more preferred. In the most preferred cases, all the binding agents and components thereof will be biocompatible.

In most cases, in order to provide a precipitate, the binding agent must be at least slightly soluble in polar solvent. Since the polar solvent will most often be removed to provide the precipitate of binding agent on the surfaces of the bone-derived elements, its non-toxicity is ordinarily not an essential criterion for its selection. However, it is usually desirable to employ a biocompatible polar solvent examples of which include water, which is generally preferred, lower alkanols such as ethanol, ketones such as acetone, ethers such as diethyl ether and mixtures of these and other polar solvents.

In some cases, a solid state crystallization or recrystallization process involving either an endogenous or exogenous metal or salt may be employed to produce the binding agent. One example of such a binding agent is the heat-activated amorphous calcium phosphate (ACP) of U.S. Pat. Nos. 6,117,456 and/or 5,683,461, the contents of which are incorporated by reference herein. In this embodiment, the ACP is added to the bone fragments prior to their being molded or formed into the desired shape. Pressure is then applied and the solid state reaction is initiated through the use of heat, moisture, the use of a catalyst or other suitable means. In this reaction, the ACP will convert to a more crystalline form of calcium phosphate, most often a poorly crystalline hydroxyapatite or a dicalcium phosphate dihydrate (DCPD). The formation of crystals of these materials serves to bind the fragments together. Alternatively, any known calcium phosphate bone cement material can be used in place of ACP, e.g., cements based upon tricalcium phosphate (TCP), tetracalcium phosphate (TTCP), the aforementioned DCPD and poorly crystalline hydroxy apatite (PCHA). In these cases, formation of crystalline bridges occurs through standard cementing reactions. Preferred ratios of ACP and known calcium phosphate bone cements to bone can range from about 0.001 to about 50% IMPLANT FOR THE TREATMENT OF BONE DEFECTS (wt/wt), preferably from about 0.01 to about 20%, and most preferably from about 0.1 to about 10%.

The binding agent can be crystalline or noncrystalline. Binding agents containing endogenous calcium that can provide a precipitate component of the implant include the crystalline and noncrystalline salts of calcium resulting from the demineralization of bone with an inorganic acid such as hydrochloric acid, sulfuric acid, nitric acid, phosphoric acid, etc., or with an organic acid such as carbonic acid, oxalic acid, trifluoroacetic acid, toluenesulfonic acid, etc. The preferred salts from which the precipitate is obtained are the chloride, sulfate and phosphate salts of calcium.

Binding agents containing an exogenous source of metal can also be crystalline or noncrystalline and can be chemically identical to any of the aforementioned calcium compounds or different therefrom in containing a metal other than calcium, e.g., inorganic and organic metal salts such as magnesium carbonate, zinc carbonate, zinc chloride and magnesium acetate, and metal oxides such as zinc oxide, magnesium oxide and iron oxide.

Bonding agents which can be used herein include metal oxides such as calcium oxide, tin oxide, barium oxide, and the like; metal hydroxides such as calcium hydroxide, magnesium hydroxide, iron hydroxide, and the like; metal salts of inorganic acids (inclusive of metal salts of substantially fully neutralized and partially neutralized inorganic acids), e.g., calcium phosphates such as tricalcium phosphate and calcium pyrophosphate, amorphous calcium phosphate, octacalcium phosphate, dicalcium phosphate dihydrate, hydroxyapatite, calcium magnesium apatite and substituted apatities such as carbonated apatite and fluorapatite, magnesium whitlockite and magnesium carbonate, and the like; metal salts of organic acids such as the calcium, magnesium and zinc salts of oxalic, acetic, citric, lactic, propionic, butyric, ethylenediaminetetraacetic, amino acids, etc., e.g., calcium oxalate, calcium acetate, magnesium acetate, zinc acetate, calcium citrate, sodium citrate, magnesium citrate, calcium lactate, calcium propionate, and the like; and, metal containing silica-based glasses such as calcium-containing silicate glasses, magnesium-containing silicate glasses, and the like.

In precipitation embodiments, the quantities of precipitate that can be deposited upon the surfaces of the bone-derived elements to achieve bonding of the latter will vary in accordance with the nature of the bonding agent making up the precipitate, the size and shape of the bone-derived elements, in particular, their surface area, and similar factors. Such quantities can be readily determined for a particular implant employing routine experimental testing. In general, the quantities of precipitate can range from about 0.1 to about 75, and preferably from about 10 to about 40, weight percent of the bone-derived elements.

The average size of the individual particles or crystals of precipitated nucleated binding agent can vary widely; in general, the average size can range from about 10 nanometers up to about 1 mm and preferably from about 0.1 to about 100 microns.

Precipitated binding agents are provided by applying a polar solvent solution of the binding agent, e.g., at a concentration of from about 10 to about 500 gm/liter, to surfaces of the bone-derived elements, either before or after forming the bone-derived elements into an aggregate which may, if desired, be configured to assume or approximate the shape of the desired implant with any final shaping being accomplished by machining. The solvent is then removed from the aggregate of bone-derived elements, e.g., by evaporation under ambient conditions or by heating at an elevated temperature, preferably one which does not significantly adversely affect the osteogenic and/or osteoconductive properties of the resulting implant, or by evaporation under vacuum with or without such heating. Evaporation of the polar solvent present on at least the surfaces of the bone-derived elements will generally be carried out to substantial completeness.

The precipitation can be enhanced by providing a rinse with a non-polar or less polar solvent. This optional use of non-polar or less polar solvent advantageously serves to decrease the solubility of the mineral phase dissolved in the polar solvent phase thereby encouraging precipitation of binding agent and at the same time causing polar solvent to be partially rinsed from the bone-derived elements. Non-polar and less polar solvents that can be used for this purpose include hydrocarbon solvents that are liquid at ambient temperatures and pressures, e.g., pentane, isopentane, hexane, isohexane, heptane, isoheptane, cyclopentane, cyclohexane, cycloheptane, and the like. These and other non-polar and less polar solvents can be added in any suitable amount to the solvent-wetted bone-derived particles to accelerate precipitation of the binding agent and wash away polar solvent as aforestated. Removal of the non-polar/ less polar solvent can then be achieved in substantially the same manner as previously described for polar solvent.

It is also within the scope of this invention to employ one or more nucleation agents in order to accelerate or encourage precipitation of binding agent in those cases where the binding agent is crystalline in character. Advantageously, this can be achieved in the case of bone-derived elements possessing surface-exposed collagen by phosphorylation of the collagen, e.g., by the procedure described in U.S. Pat. No. 5,814,328, the contents of which are incorporated by reference herein. Phosphorylation of the surface-exposed collaged results in the production of nucleation sites which serve to promote crystal formation and, consequently, rapid precipitation of crystals of binding agent from solution. Additionally, bone elements can be prepared to micrometer or nanometer size and can be added as nucleators. Also, the external surface of bone particles can be treated mechanically or chemically to "tease" bone particle surfaces thereby providing additional binding sites for crystal precipitation.

In some embodiments while evaporation of solvent is taking place, the aggregate of bone-derived elements can be subjected to mechanical pressures, e.g., on the order of from about 500 to about 100,000 psi, and preferably from about 2,000 to about 20,000 psi, for part or all of the evaporation period and even beyond. This application of pressure generally provides an improvement in one or more mechanical properties of the resulting implant. Pressure may also be used to induce crystal nucleation. For instance, soluble mineral can be added to the solution beyond its saturation point. A higher pressure can then be applied to the solution allowing more of the mineral to enter solution. The solution, saturated at the higher pressure, is then brought into contact with the bone and penetrates it. Finally, the pressure is reduced inducing crystal nucleation and formation of precipitate from the (now) supersaturated solution.

The solvent solution of binding agent can be provided on the surfaces of the bone-derived elements by one of two basic procedures depending on whether endogenous calcium or an exogenous source of metal is present therein.

In the case of a binding agent containing endogenous calcium, the polar solvent solution of the binding agent can be formed on the surfaces of the bone-derived elements in situ employing known and conventional acid demineralization methods, e.g., those described in Reddi et al., *Proc. Nat. Acad. Sci.* 69, pp 1601–1605 (1972), incorporated herein by reference. The strength of the aqueous acid solution, the shape of the bone and the duration of the demineralization treatment will determine the extent of demineralization which can range from superficial to substantially complete. Reference in this regard may be made to Lewandrowski et al., *J Biomed Materials Res.*, 31, pp 365–372 (1996), also incorporated herein by reference. Thus, e.g., superficial, or surface, demineralization of bone particles with about 0.5ml/g to about 10 ml/g aqueous solution of 0.6N hydrochloric acid or from about 25 to about 50 weight percent aqueous phosphoric acid for from 1 to about 30 minutes will generally result in the presence of an aqueous solution of, respectively, calcium chloride or calcium phosphate, on the demineralized surfaces of the bone particles. Following evaporation of solvent to cause precipitation of calcium salt, the latter will be present to function as binding agent for the aggregate of bone particles. As previously described, a nucleation agent can be introduced into the system and/or the polar solvent solution can be rinsed with a non-polar and/or less polar solvent to enhance precipitation of binding agent. It is also within the scope of this invention to prepare treated components which will recruit binding elements in situ from the surrounding body fluid of the recipient.

An enhancement of the foregoing method of providing endogenous calcium binding agent, one that can also be applied to the method of providing exogenous binding agent, infra, is to first treat the surface of the bone-derived particles with a substantially neutral or basic solution of a divalent (or higher valent) metal. The divalent or higher valent metal can also be applied as powder in the form of a metal salt. The goal is to add additional metal to the bone particles (including the surface and accessible pores) before any of the endogenous calcium is dissolved by treatment with acid. The pretreated bone is then subjected to the previously described endogenous treatment. This pretreatment process can lead to the formation of a more insoluble precipitate and thus a more stable binding effect.

Another enhancement of the foregoing endogenous method is to contact the bone particles while they are still wet with acid solution with a neutralizing (basic) solution. Preferably, the neutralizing solution contains dissolved metal ions that will precipitate together with the endogenous salt.

Yet another method of providing an endogenously derived precipitate of binding agent is to contact the bone-derived elements with aqueous sodium silicate (water glass) to provide a precipitate of calcium silicate supplemented, if desired, with an exogenously derived binding agent.

When the precipitation of an exogenous binding agent is chosen as the binding means, deposition of a polar solvent solution of the binding agent can be achieved, e.g., by immersing a quantity of bone-derived elements within an excess of the solution and after a few minutes, draining the excess solution and thereafter subjecting the solution to evaporation conditions as aforedescribed to provide the precipitate. As previously described, a non-polar/less polar solvent and/or a nucleation agent can be used to enhance the precipitation of binding agent and removal of the polar solvent. The foregoing exogenous method can also be enhanced by first treating the surfaces of the bone-derived elements with an acid capable of forming a salt(s) with the endogenous metals in the bone, particularly calcium, in order to provide a more highly mineralized surface that is more compatible with the exogenous binding agent.

As stated above, adjacent bone-derived elements constituting the aggregate are bonded to each other through engagement with the precipitate present on surfaces of the elements. As shown in the photomicrographs of FIGS. 1–3,the bonding is of two general kinds, namely, mechanical interlocking of mutually contacting precipitate and bridge-like structures of precipitate spanning the gaps between adjacent bone-derived elements.

FIGS. 1–3were obtained by conventional scanning electron microscopy (SEM) techniques to provide a 5,000 magnification of each bone sample.

Figure 1:
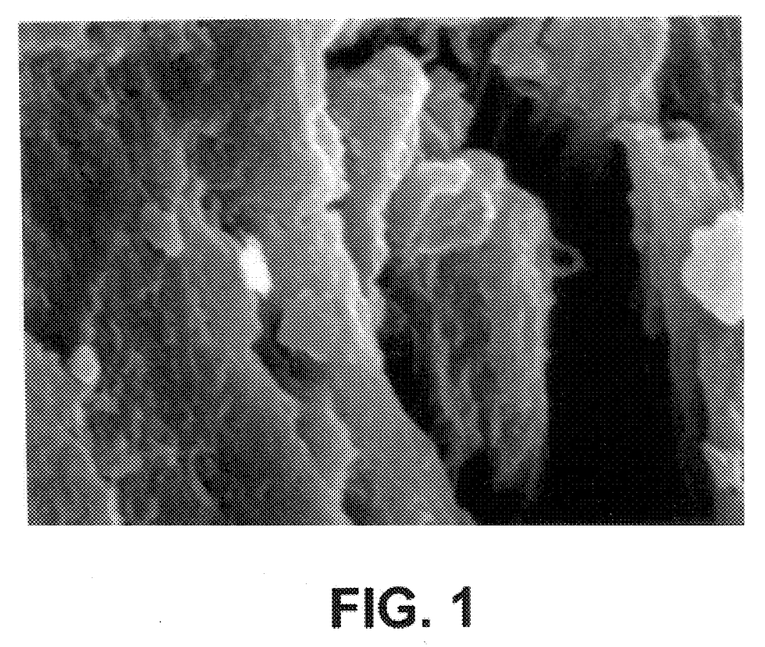
FIG. 1 is a photomicrograph showing the surface of natural nondemineralized human bone; and, FIGS. 2 and 3 are photomicrographs showing the surfaces of demineralized human bone possessing precipitates of nonadhesive binding agent distributed thereon in the form of crystals (FIG. 2) and as a bridge-like structure between adjacent bone particles (FIG. 3).

FIG. 1 shows the surface of untreated bone and is presented for comparison purposes.

Figure 2:
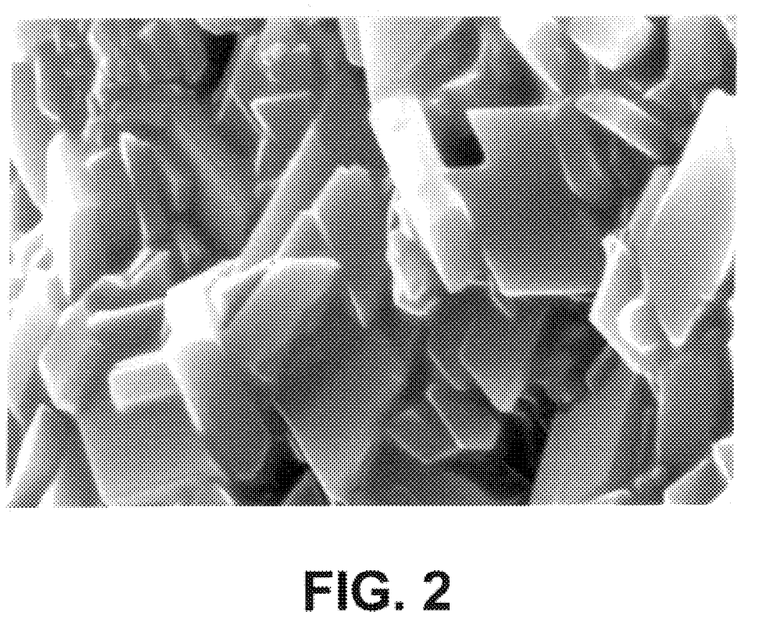
Figure 3:
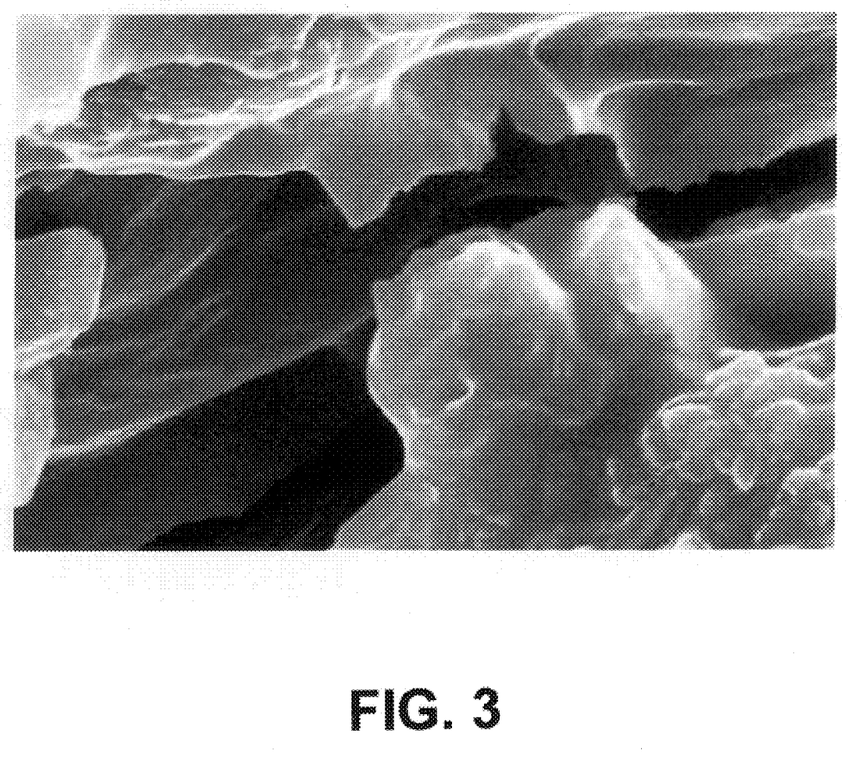

FIG. 2 shows the surface of bone to which has been applied an endogenous precipitate of crystalline material, believed to be dicalcium phosphate dihydrate, obtained by contacting the bone surface with 25 weight percent aqueous phosphoric acid for 5 minutes followed by rinsing and evaporation of the water solution under ambient conditions. FIG. 2 clearly shows the crystalline nature of the precipitate, the sharply-defined planar surfaces of individual irregularly formed crystals being available to mechanically interlock with the similarly structured crystals on the surface of an adjacent piece of bone.

In FIG. 3, precipitate formed by the same surface demineralization procedure used for the treatment of the bone of FIG. 2 has formed a bridge-like structure between adjacent bone elements binding the bone elements to each other. The bridge-like structure appears to have fractured and is believed to be an artifact of the procedure employed for the preparation of the SEM sample.

In addition to containing bone-derived elements, the implant of this invention can optionally possess one or more other components such as reinforcing particles, fibers, fillers, growth factors, trophic factors, adhesives, plasticizers, flexibilizing agents, therapeutic agents, biostatic/biocidal agents, substances imparting radiopacity, particles, fibers, metallic meshes, and the like. Examples of reinforcing particles include filly mineralized cortical and cancellous bone, and partially demineralized cortical and cancellous bone in any form, including particles, sheets and shaped bone pieces; graphite or pyrolytic carbon. Examples of fillers include mineral material such as hydroxyapatite, tricalcium phosphate and other calcium salts, graphite or pyrolytic carbon, bioglass or other bioceramic or natural or synthetic polymers, e.g., bioabsorbable/bioerodable polymers such as tyrosine polycarbonate, polyarylates, polypropylene fumarate diacrylates and their derivatives, polyglycolide, polylactide, glycolide-lactide copolymer, and the like. Additional useful bioabsorbable/bioerodable polymers and their preparation are described in "Handbook of Biodegradeable Polymers", A. J. Domb, J. Kost, D. M. Wiseman, eds., Harwood Academic Publishers, 1997, the contents of which are incorporated by reference herein. Preformed nonbioabsorbable polymers can also be added to the implant and include such materials as polymethyl methacrylate, polytetrafluoroethylene, polyurethane, polyethylene, polyamide, and the like. Plasticizers, flexibilizing agents and hydration facilitating agents such as glycerol, monacetin, diacetin, and mixtures thereof, can also be employed. Suitable biostatic/biocidal agents include antibiotics, povidone, sugars, and mixtures thereof; suitable surface agents include the biocompatible nonionic, cationic, anionic and amphoteric surfactants, and mixtures thereof. The implant can also possess bone-growth inducing substances which include any of a variety of medically and/or surgically useful substances such as those described below.

The implant can possess one or more cavities which, if desired, can communicate with the surface of the implant through pores, apertures, perforations or channels provided for this purpose and range in average diameter from a few microns to several millimeters. Such cavities and their associated pores, apertures, perforations, and channels can be partially or completely filled with one or more medically/surgically useful substances which promote or accelerate new bone growth or bone healing due, e.g., to some osteogenic, osteoconductive and/or osteoconductive effect. Useful substances of this kind which can be incorporated into the implant of this invention (either within the pores or co-precipitated with the binding agent) include, e.g., collagen, insoluble collagen derivatives, etc., and soluble solids and/or liquids dissolved therein. Particularly useful are therapeutic agents, e.g., antiviral agents, especially those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextrose, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone, low levels of strontium, zinc or magnesium, autogenous tissues such as blood, serum, soft tissue, bone marrow, etc.; bioadhesives, bone morphogenetic proteins (BMPs), transforming growth factor (TGF-beta), insulin-like growth factor (IGF-1, IGF-2); growth hormones such as somatotropin; bone digestors; antitumor agents; immunosuppressants; angiogenic agents such as vascular endothelial growth factor (VEGF) or basic fibroblast growth factor (BFGF); permeation enhancers, e.g., fatty acids and fatty acid esters such as laureate, myristate, phosphatidyl choline, phosphatidyl serine, phosphatidyl ethandiamine and stearate monoesters of polyethylene glycol, enamine derivatives, alpha-keto aldehydes, etc.; and, nucleic acids. These and similar medically/surgically useful substances can be incorporated into the implant of this invention or any of its constituent bone-derived elements or other components during any stage of the assembly of the implant. Suitable methods of incorporation include coating, immersion saturation, packing, etc. The amounts of medically/surgically useful substances utilized can vary widely with optimum levels being readily determined from the literature or in other specific cases by routine experimentation.

Implants of any desirable size and/or configuration can be provided, e.g., by machining or other mechanical shaping of the base aggregate, e.g., by cutting, grinding, milling, shaving, carving, etc., or by any of a variety of molding techniques, e.g., press-molding as previously mentioned. Computerized modeling of a specific implant followed by computerized control of the shaping of the implant can be used to provide an intricately shaped implant which is thereafter custom-fitted to the intended bone repair site with great precision. Thus, e.g., known and conventional computed tomography (CT) and computer modeling methods can be used to achieve custom design of the implant of this invention. Reference may be made, in this regard, to U.S. Pat. No. 5,086,401, the contents of which are incorporated by reference herein.

It is within the scope of the invention to supplement or increase the shape retaining and/or mechanical strength characteristics of the implant, e.g., by the addition of mechanical fasteners such as pins, screws, dowels, etc., which can be fabricated from natural or synthetic materials and bioabsorbable as well as non-bioabsorbable materials, by the use of laser tissue welding or ultrasonic bonding, and so forth. In those embodiments of the implant which are assembled from relatively large bone-derived elements such as sheets, such elements can be provided with mechanically interengaging features, e.g., tongue-and-groove or mortise-and-tenon features, mutually engaging serrated surfaces, etc., which facilitate their assembly into the final product and/or bond the bone-derived elements to each other in a more secured fashion.

The implant herein is intended to be applied at any site where it may be beneficial to provide a structural or therapeutic function. In one preferred example, the implant is used at a bone defect site, e.g., one resulting from injury, defect brought about during the course of surgery, infection, malignancy or developmental malformation. The implant, suitably sized and shaped as required, can be utilized as a graft or replacement in a wide variety of orthopaedic, neurosurgical, podiatric, plastic and reconstructive, trauma and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. Specific bones which can be repaired or replaced with the implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ileum, ischium, pubis, femur, tibia, fibula, patella, calcaneus, tarsal, and metatarsal bones. Non-orthopedic uses include biocompatible structural implants for the support, reinforcement or segregation of organs or issues as might be useful in tissue engineering or cell therapy applications. In these cases, the implant strength, biocompatibility, and resorption/remodeling properties of the implant may be particularly advantageous.

The following examples are illustrative of the implant of this invention and its method of manufacture.

EXAMPLE 1

The samples of bone aggregate prepared herein contained a mixture of bone particles consisting of 50 weight percent fibers (average size of 500–850 microns), 30 weight percent particles (average size of 500–850 microns) and 20 weight percent powder (average size of 300–500 microns). The mixtures were defatted with a chloroform/methanol (50/50) solution, stirred overnight and thoroughly dried prior to being formed into aggregates. The bone particles were surface-demineralized with 25 weight percent aqueous phosphoric acid, the excess liquid was drained and the wetted bone particles were remixed thoroughly and then placed into compression sleeves. The sleeves were compressed to apply a pressure of 11,500 psi to each of the samples which were thereafter heated to 45° C. and held at the pressure for 1 and 24 hours, respectively. The samples were then removed from the sleeves and placed in a drying oven at 45° C. for 24 hours. This method had 2 observations generating 3 samples each. Mechanical strength testing of the samples of bone aggregate was performed on one dry and two wet samples (24 hours SBF and 7 days SBF).

The experiments yielded dry strength results of 103 and 140 MPa, the 24 hour wet strengths were 0.6 and 7.2 MPa and the 7 day wet strengths were 1.2 and 7.4 MPa. Both of the wet stability samples maintained strengths greater than 1 MPa after the full 7 days in SBF and both gained strength between the 24 hour and 7 day time periods. The samples that were compressed for the longest period of time (24 hours) had strengths comparable to the low range strength of cancellous bone at the 24 hour time point and increased slightly at the 7 day time point.

EXAMPLE 2

The samples of bone aggregate prepared herein employed a mixture of bone material consisting of 50 weight percent fibers (average size of 500–850 microns), 30 weight percent particles (average size of 500–850 microns) and 20 weight percent powder (average size of 300–500 microns). The mixture was defatted with a chloroform/methanol (50/50) solution, stirred overnight and thoroughly dried prior to bonding into aggregates. The mixture of bone material was substantially completely demineralized with 1 N HCl and thoroughly rinsed with deionized water. The mixture was then rinsed with a saturated calcium phosphate solution. The excess liquid was removed, the mixture was remixed thoroughly and samples placed into compression sleeves. The sleeves were compressed to apply various pressures (1000, 3000, 5000 and 11,500 psi), heated to various temperatures (23, 34 and 45° C.) and held at the two previous pressure conditions for various lengths of time (1, 7, 14 and 24 hours). The samples were then removed from the sleeves and placed in a drying oven at 45° C. for 24 hours. The screening and statistical combination of all considered variables equated to 12 total observations generating 3 samples each. Mechanical strength testing was performed on each observation, one dry and two wet samples (24 hours SBF and 7 days SBF).

The data collected from the "screening" and "statistical" DOE methods yielded dry strength results that ranged between 20 to 125 MPa, the 24 hour wet strengths between <1 MPa to 5.8 MPa and the 7 day wet strengths between <1 MPa (of which there were 5 total) to 5.2 MPa. The samples that had strengths under 1 MPa after 7 days in simulated body fluid were all formed at 23° C. and/or 1 hour. Of the remaining samples, one of the samples gained strength, eight lost strength and one remained unchanged between the 24 hour and 7 day time points. The statistical analysis of the data showed a significant forming interaction involving all three of the variables tested (forming pressure, length of forming time and forming temperature).

EXAMPLE 3

The samples of bone aggregate prepared herein employed a mixture of bone material consisting of 50 weight percent fibers (average size of 500–850 microns), 30 weight percent particles (average size of 500–850 microns) and 20 weight percent powder (average size of 300–500 microns). The mixture was defatted with a chloroform/methanol (50/50) solution, stirred overnight and thoroughly dried prior to being bonded into samples of aggregate. The mixture of bone material was substantially completely demineralized with 1N HCl and thoroughly rinsed with deionized water. The excess liquid was removed, the mixture was remixed thoroughly and then placed into compression sleeves. The sleeves were then compressed to various pressures (1000, 3000 and 5000 psi), heated to various temperatures (23, 34 and 45° C.) and held at the two previous pressure conditions for various lengths of time (1, 7 and 14 hours). The samples were then removed from the sleeves and submerged in a solution of an exogenous source of acidic calcium phosphate for various time periods (1, 3 and 5 hours) while adjusting the pH to 7. When each individual sample reached the desired pH, it was removed from the calcium phosphate solution and placed in a drying oven at 45° C. for 24 hours. The statistical combination of all considered variables equated to 18 total observations generating 3 samples each. Mechanical strength testing was performed on each observation, one dry and two wet samples (24 hours SBF and 7 days SBF).

The data collected from this "statistical" DOE method yielded dry strength results that ranged between 8.7 to 138 MPa. The wet strengths for the 24 hour time period ranged between 0.9 to 15.9 MPa and the wet strengths for the 7 day time period ranged between 0.8 to 5.7 MPa. All of the wet stability samples survived the full 7 days in SBF and tended to decrease in strength between the 24 hour and 7 day test points. Fifteen of the samples lost strength and only one remained unchanged between the 24 hour and 7 day test points. The statistical analysis of the data showed a significant forming interaction involving all four variable tested (forming pressure, length of forming time, forming temperature and pH adjustment time).

EXAMPLE 4

Two cortical bone slabs were cut from bovine bone and thereafter machined to provide mating serrated surfaces on one side. Matching serrated surfaces of the two cortical bone plates were blotted dry of moisture and then coated with 0.6N HCl to achieve superficial demineralization of the surfaces which, as a result, became coated with aqueous calcium chloride. The serrated surfaces of the plates were then mated to provide a composite which was then air-dried for approximately 2 hours. After drying, an attempt was made to shear the plates apart by hand, an effort that required significant force. Only the outer portion of the bone plate-contacting surfaces appeared to have fully dried.

Using the foregoing method, three clamped serrated bone plate specimens were prepared and air-dried overnight. The third specimen was subjected to a 19 hour freeze-drying cycle. One of the air-dried samples was forced apart (in the dried state) by hand with some effort. The other air-dried specimens were allowed to re-hydrate in physiological saline for 10 minutes after which it took much less force to separate the plates by hand. Plates in the freeze-dried specimen fell apart with no applied force after the freeze-drying process.

Another bone plate specimen was provided as above with the exception of being painted with 0.6N phosphoric acid. The clamped specimen was dried overnight. A white layer of calcium phosphate filled all gaps between the plates of the specimen when dry. Upon unclamping and re-hydration in saline for 15 minutes, the layers were easier to separate than any of the previously prepared specimens but were more difficult to separate than the re-hydrated HCl-bonded specimens.

Another bone plate specimen was provided as above with the exception of being coated with 0.6N phosphoric acid saturated with hydroxyapetite (HA). The clamped specimen was dried overnight. A white layer of crystals, thought to be dicalcium phosphate dihydrate, filled all gaps between the plates of the specimen when dry. The specimen sheared apart fairly easily in the dry state.

EXAMPLE 5

Three groups of fiber-like bone particles were prepared. The first group of bone particles were prepared as described in Example 1 including phosphoric acid pre-treatment. A second fully demineralized group of bone particles were prepared as described in Example 2. A third group of partially demineralized bone particles were prepared by treating the particles with 0.6N HCl (2mL/gm) for 10–15 minutes at room temperature. The demineralization solution is removed and the fibers were rinsed with distilled water and blotted dry. Particles prepared by this last method had a Ca content of approximately 20–25% gm/cc.

EXAMPLE 6

The three groups of fibrous bone particles described in Example 5, supra, are mixed with a dry calcium phosphate powder in accordance with the parameters indicated in Table 1. Following mixing, all samples are divided into two parts and molded at either 6,000 psi or 50,000 psi. for 24 hrs in the compression sleeve of Example 3. Following molding, samples are tested for compression strength and duplicate samples are implanted in both a canine metaphyseal defect model and a sheep spine fusion model.

TABLE 1

| Calcium phosphate (CaP) | CaP Amount (wt %) | Bone Amount (wt %) | $HPO_4$ Pretreatment |
|---|---|---|---|
| Lyophilized ACP as | 0.1 | 99.9 | Yes |
| described in U.S. Pat. | 1 | 99 | No |
| No. 5,782,971 | 10 | 90 | Yes |
|  |  |  | No |
|  |  |  | Yes |
|  |  |  | No |
| Lyophilized DCPD | 0.1 | 99.9 | Yes |
| (particle size = .01–.1 mm) | 1 | 99 | No |
| as described in U.S. Pat. | 10 | 90 | Yes |
| No. 6,117,456 |  |  | No |
|  |  |  | Yes |
|  |  |  | No |
| ACP/DCPD or | 0.1 | 99.9 | Yes |
| ACP/PCHA calcium | 1 | 99 | No |
| phosphate bone cement as | 10 | 90 | Yes |
| described in U.S. Pat. |  |  | No |
| No. 6,117,456 |  |  | Yes |
|  |  |  | No |
| TTCP calcium phosphate | 0.1 | 99.9 | Yes |
| bone cement as described | 1 | 99 | No |
| in U.S. Pat. No. | 10 | 90 | Yes |
| 5,997,624 |  |  | No |
|  |  |  | Yes |
|  |  |  | No |
| Amorphous calcium | 0.1 | 99.9 | Yes |
| phosphate as described in | 1 | 99 | No |
| U.S. Pat. No. 5,783,217 | 10 | 90 | Yes |
|  |  |  | No |
|  |  |  | Yes |
|  |  |  | No |
| TCP Bone cement powder | 0.1 | 99.9 | Yes |
| as described in U.S. Pat. | 1 | 99 | No |
| No. 5,782,971 | 10 | 90 | Yes |
|  |  |  | No |
|  |  |  | Yes |
|  |  |  | No |
| Bone cement as described | 0.1 | 99.9 | Yes |
| in U.S. Pat. No. | 1 | 99 | No |
| 5,605,713 | 10 | 90 | Yes |
|  |  |  | No |
|  |  |  | Yes |
|  |  |  | No |
| Poorly crystalline HA as | 0.1 | 99.9 | Yes |
| described in U.S. Pat. | 1 | 99 | No |
| No. 6,117,456 | 10 | 90 | Yes |
|  |  |  | No |
|  |  |  | Yes |
|  |  |  | No |

Samples are recovered at 6, 12 and 24 weeks, and the extent of implant remodeling and new bone formation is determined.

What is claimed is:

1. An implant which comprises a solid aggregate of bone-derived elements in which the surfaces of individual bone-derived elements possess one or more binding agents selected from the group consisting of metal oxide, metal hydroxide, metal salt of an inorganic acid, metal salt of an organic acid and metal-containing silica-based glass, the binding agent possessing at least slight solubility in a polar solvent, adjacent bone-derived elements in the aggregate being bonded to each other through engagement with the binding agent.

2. The implant of claim 1 wherein at least a major amount by weight of the bone-derived elements exhibit osteogenic, osteoconductive and/or osteoinductive properties.

3. The implant of claim 1 wherein the bone-derived elements are particles, powders, granules, fibers, strips, sheets and/or large pieces of xenogenic, allogenic, transgenic, tissue engineered or autologous cortical and/or cancellous bone.

4. The implant of claim 1 in which the metal constituent of the binding agent is endogenous to bone.

5. The implant of claim 4 in which the endogenous metal is calcium.

6. The implant of claim 4 additionally containing at least one binding agent whose metal constituent is exogenous to bone.

7. The implant of claim 6 wherein the endogenous metal is calcium and the exogenous metal is selected from the group consisting of calcium, magnesium, barium, iron, zinc and tin.

8. The implant of claim 4 wherein the binding agent is a compound of endogenous calcium selected from the group consisting of calcium chloride, calcium sulfate, calcium phosphate, calcium oxalate and calcium silicate.

9. The implant of claim 1 in which the metal constituent of the binding agent is exogenous to bone.

10. The implant of claim 9 wherein the exogenous metal is selected from the group consisting of calcium, magnesium, barium, iron, zinc and tin.

11. The implant of claim 10 wherein the binding agent is an oxide, a hydroxide or a phosphate, chloride, nitrate, sulfate, silicate, carbonate, oxalate, acetate, citrate, lactate, propionate, butyrate, aminoacid carboxylate or ethylenediamine-tetraacetate salt.

12. The osteimplant of claim 1 wherein the metal constituent of the binding agent is a divalent, trivalent or higher valent metal.

13. The implant of claim 1 further comprising at least one component selected from the group consisting of reinforcing particles, reinforcing fibers, fillers, growth factors, trophic factors, adhesives, plasticizers, flexibilizing agents, cellular material, genetic material, calcification controlling agents, hydration facilitating agents, biostatic agents, biocidal agents, polymers, inorganic compounds, substances imparting radiopacity and metallic meshes.

14. The implant of claim 1 having the configuration of a bone or bone segment.

15. The implant of claim 1 wherein bone-derived elements in the aggregate are bonded to each other through interlocking engagement of particles of binding agent present on the mutually-contacting surfaces of adjacent bone-derived elements and/or by bridge-like structures of binding agent between adjacent bone-derived elements.

16. A method of making an implant made up of a solid aggregate of bone-derived elements which comprises:
   a) contacting the surfaces of a quantity of bone-derived elements with a polar solvent solution of one or more binding agents selected from the group consisting of metal oxide, metal hydroxide, metal salt of an inorganic acid, metal salt of an organic acid and metal-containing silica-based glass, the binding agent possessing at least slight solubility in a polar solvent;
   b) forming the bone-derived elements into an aggregate prior to or following contacting step (a); and,
   c) removing polar solvent from the aggregate of bone-derived elements to provide the implant, the bone-derived elements in the implant possessing binding agent with adjacent bone-derived elements being bonded to each other through engagement with the binding agent.

17. The method of claim 16 wherein at least a major amount by weight of the bone-derived elements exhibit osteogenic, osteoinductive and/or osteoinductive properties.

18. The method of claim 16 wherein the polar solvent solution of binding agent is an aqueous solution of a calcium salt or silica-based glass formed in situ by contacting the surfaces of the bone-derived elements with an aqueous inorganic acid, aqueous organic acid or aqueous sodium silicate.

19. The method of claim 18 wherein prior to contacting the surfaces of bone-derived elements with aqueous acid or aqueous silicate, a substantially neutral or basic solution of a divalent or higher valent metal compound or said metal compound in pulverulent form is applied to the surfaces of the bone-derived elements.

20. The method of claim 18 wherein prior to removal of polar solvent, the bone-derived elements wetted with aqueous acidic solution of calcium salt is contacted with a neutralizing solution, optionally containing dissolved metal ions, that upon removal of polar solvent form a coprecipitate with the calcium salt precipitate.

21. The method of claim 16 wherein polar solvent is removed by evaporation at ambient pressure and temperature, at reduced pressure, or at an elevated temperature with or without a reduced pressure.

22. The method of claim 16 wherein polar solvent is removed by evaporation at elevated pressure with or without elevated temperature.

23. The method of claim 16 wherein the binding agent is precipitated from a supersaturated solution.

24. The method of claim 16 wherein polar solvent is removed by contacting the polar solvent with non-polar solvent and/or less polar solvent.

25. The method of claim 16 wherein the binding agent is crystalline, precipitation of the binding agent from the polar solvent being enhanced by contact of the polar solvent solution of binding agent with a nucleation agent.

26. The method of claim 16 wherein at least some of bone-derived elements possess surface-exposed collagen which has been phosphorylated prior to contacting the bone-derived elements with the polar solvent solution of binding agent.

27. The method of claim 26 wherein polar solvent is removed by contacting the polar solvent with non-polar solvent and/or less polar solvent.

28. The method of claim 16 wherein the binding agent is crystalline, precipitation of the binding agent from the polar solvent being enhanced by adjustment of the pH of the polar solvent to a range where solubility of the binding agent is reduced.

29. The method of claim 16 wherein at least some of bone-derived elements are treated to expose collagen at their surfaces.

30. The method of claim 16 wherein during the step of removing polar solvent, the aggregate of bone-derived elements is optionally subjected to mechanical pressure.

31. The method of claim 16 wherein the binding agent is selected from the group consisting of calcium chloride, calcium sulfate, calcium phosphate, calcium oxalate and calcium silicate which has been formed in situ.

32. The method of claim 31 wherein autogenous bone is additionally used.

33. The method of claim 16 wherein the binding agent contains exogenously-derived metal.

34. The method of claim 16 wherein the aggregate of bone-derived elements is formed into a shaped mass.

35. The method of claim 34 wherein the shaped mass is formed in a mold to which pressure is applied during the removal of polar solvent.

36. The method of claim 35 wherein the shaped mass is machined to final configuration following the removal of polar solvent.

37. A method of making an implant made up of a solid aggregate of bone-derived elements which comprises contacting the surfaces of a quantity of bone-derived elements with a dry metal salt and initiating a crystallization reaction involving the salt to provide a biocompatible binding agent of crystallized salt on the surfaces of the bone-derived elements, adjacent bone-derived elements being bonded to each other through engagement with the binding agent.

38. The method of claim 37 wherein at least a major amount by weight of the bone-derived elements exhibit osteogenic, osteoconductive or osteoinductive properties.

39. The method of claim 37 wherein the dry metal salt is amorphous calcium phosphate.

* * * * *